US012778984B2

(12) United States Patent
Li et al.

(10) Patent No.: US 12,778,984 B2
(45) Date of Patent: Nov. 3, 2026

(54) CHIMERIC ANTIGEN RECEPTOR FUSION PROTEIN CO-EXPRESSING IL-7 AND CCR2b, AND APPLICATION THEREOF

(71) Applicant: GUANGZHOU BIO-GENE TECHNOLOGY CO., LTD, Guangzhou (CN)

(72) Inventors: Guangchao Li, Guangzhou (CN); Min Luo, Guangzhou (CN); Wen Ding, Guangzhou (CN); Xuejun Wang, Guangzhou (CN)

(73) Assignee: GUANGZHOU BIO-GENE TECHNO, Guangzhou (CN)

(*) Notice: Subject to any disclaimer, the term of this patent is extended or adjusted under 35 U.S.C. 154(b) by 553 days.

(21) Appl. No.: 18/278,163

(22) PCT Filed: Mar. 30, 2021

(86) PCT No.: PCT/CN2021/083847

§ 371 (c)(1),
(2) Date: Aug. 21, 2023

(87) PCT Pub. No.: WO2022/174498

PCT Pub. Date: Aug. 25, 2022

(65) Prior Publication Data

US 2024/0122982 A1 Apr. 18, 2024

(30) Foreign Application Priority Data

Feb. 22, 2021 (CN) ......................... 202110196691.7

(51) Int. Cl.

| | |
|---|---|
| ***A61K 35/17*** | (2025.01) |
| ***A61K 40/11*** | (2025.01) |
| ***A61K 40/31*** | (2025.01) |
| ***A61P 35/00*** | (2006.01) |
| ***C07K 14/54*** | (2006.01) |
| ***C07K 14/705*** | (2006.01) |
| ***C07K 14/715*** | (2006.01) |
| ***C07K 16/30*** | (2006.01) |
| *A61K 39/00* | (2006.01) |

(52) U.S. Cl.

CPC .............. *A61K 35/17* (2013.01); *A61K 40/11* (2025.01); *A61K 40/31* (2025.01); *A61P 35/00* (2018.01); *C07K 14/5418* (2013.01); *C07K 14/70517* (2013.01); *C07K 14/7158* (2013.01); *C07K 16/3084* (2013.01); *A61K 2039/5156* (2013.01); *A61K 2239/15* (2023.05); *C07K 2317/622* (2013.01); *C07K 2319/02* (2013.01); *C07K 2319/03* (2013.01)

(58) Field of Classification Search

None

See application file for complete search history.

(56) References Cited

U.S. PATENT DOCUMENTS

| | | | | |
|---|---|---|---|---|
| 10,316,102 | B2 * | 6/2019 | Tamada | ................ A61K 35/26 |
| 2017/0056448 | A1 | 3/2017 | Glick et al. | |
| 2017/0291953 | A1 | 10/2017 | Tamada et al. | |
| 2019/0016820 | A1 | 1/2019 | Pule et al. | |
| 2022/0280566 | A1 | 9/2022 | Wang et al. | |

FOREIGN PATENT DOCUMENTS

| | | | |
|---|---|---|---|
| CN | 108218999 | A | 6/2018 |
| CN | 108715859 | A | 10/2018 |
| CN | 108728460 | A | 11/2018 |
| CN | 109266667 | A | 1/2019 |
| CN | 110684739 | A | 1/2020 |

OTHER PUBLICATIONS

Moon, E.M., et al. (2011) "Expression of a Functional CCR2 Receptor Enhances Tumor Localization and Tumor Eradication by Retargeted Human T cells Expressing a Mesothelin-Specific Chimeric Antibody Receptor", Clinical Cancer Research, 17:4719-4730.

Craddock, J.A., et al. (2010) "Enhanced Tumor Trafficking of GD2 Chimeric Antigen Receptor T Cells by Expression of the Chemokine Receptor CCR2b", J. Immunother., 33:780-788.

* cited by examiner

*Primary Examiner* — Meera Natarajan
(74) *Attorney, Agent, or Firm* — Kagan Binder, PLLC

(57) ABSTRACT

A chimeric antigen receptor fusion protein co-expressing IL-7 and CCR2b, and application thereof are provided. The fusion protein includes a chimeric antigen receptor, a 2A peptide, IL-7, a 2A peptide and CCR2b which are sequentially linked in series.

9 Claims, 9 Drawing Sheets

Specification includes a Sequence Listing.

CHIMERIC ANTIGEN RECEPTOR FUSION PROTEIN CO-EXPRESSING IL-7 AND CCR2b, AND APPLICATION THEREOF

CROSS-REFERENCE TO RELATED APPLICATIONS

This application is a U.S. national phase application under 35 U.S.C. § 371 which claims priority to International Patent Application No. PCT/CN2021/083847, filed on Mar. 30, 2021, which claims the priority benefit of Chinese Patent Application No. 202110196691.7, filed on Feb. 22, 2021. The contents of the above identified applications are hereby incorporated herein in their entireties by reference.

SEQUENCE LISTING

This application contains a Sequence Listing in computer readable form submitted via USPTO Patent Center. The entire contents of the ASCII text file entitled "ACL0142US_Sequence_Listing_V2.txt" created on Nov. 30, 2023, and having a size of 30,578 bytes, is incorporated herein by reference.

TECHNICAL FIELD

The present disclosure relates to the field of biomedicine, and specifically to a chimeric antigen receptor fusion protein co-expressing IL-7 and CCR2b, and application thereof.

BACKGROUND

Recently, a biological therapy for a tumor has become a new therapeutic method followed surgery therapy and chemoradiotherapy. The biological therapy is a kind of therapy that uses biological methods to adjust the "anti-cancer mechanism" of an organism, thereby making it balanced and stable. The biological therapy includes a cell therapy, a gene therapy, an antibody therapy and a cytokine therapy.

Among them, a chimeric antigen receptor T-cell (CAR-T) therapy is a promising one. In the basic design, a chimeric antigen receptor (CAR) includes a tumor associated antigen-binding region that is usually derived from the single-chain variable fragment (scFv) segment of an antigen-binding region of an antibody, an extracellular hinge region, a transmembrane region, and an intracellular signaling region. Upon such a receptor is expressed by T cells, a single fusion molecule specifically binds to an antigen and activates T cells, so that the T cell modified by the chimeric antigen receptor has the specificity of an antibody and the cytotoxic effect of effector T cells. CAR, once bound to tumor-associated antigen (TAA), can activate T cells through CD3 or an intracellular region of high-affinity receptor FceR1, exhibiting CAR-dependent cell killing, proliferation and cytokine release. Meanwhile, CAR-T cells can be expanded by more than 1000 times. It has been found in clinical trials that high expression level of CAR can still be detectable in patients in six months after inputting CAR-T cells. In short, CAR-T cells have targeting ability, killing activity and persistence superior to those of conventionally used immune cells.

CAR-T cells have remarkable therapeutic effect on cancer immunotherapy, especially on the treatment of leukemia. However, there are two major problems that need to be solved in the treatment of a solid tumor by CAR-T, including survival of CAR-T cells in a solid tumor site and effective migration of CAR-T cells to a solid tumor site.

SUMMARY

In a first aspect, the present disclosure relates to a fusion protein including a chimeric antigen receptor The fusion protein includes a chimeric antigen receptor, a 2A peptide, IL-7, a 2A peptide and CCR2b which are sequentially linked in series.

In a second aspect, the present disclosure relates to an isolated nucleic acid, expressing the fusion protein as described above.

In a third aspect, the present disclosure relates to a vector, including the nucleic acid as described above.

In a fourth aspect, the present disclosure relates to a T cell, including the nucleic acid as described above or the vector as described above.

In a fifth aspect, the present disclosure relates to a composition, including the T cell as described above and a pharmaceutically acceptable carrier.

In a sixth aspect, the present disclosure relates to use of the T cell as described above or the composition as described above in the preparation of a medicament for preventing and/or treating a solid tumor.

BRIEF DESCRIPTION OF THE DRAWINGS

In order to illustrate the embodiments of the present disclosure or the technical solutions of the prior art more clearly, the drawings that need to be used in the description of the specific embodiments or the prior art will be described briefly below. Apparently, the following described drawings are merely for some embodiments of the present disclosure, and other drawings can also be derived by those of ordinary skill in the art based on these drawings without any creative effort.

DETAILED DESCRIPTION

Figure 1:
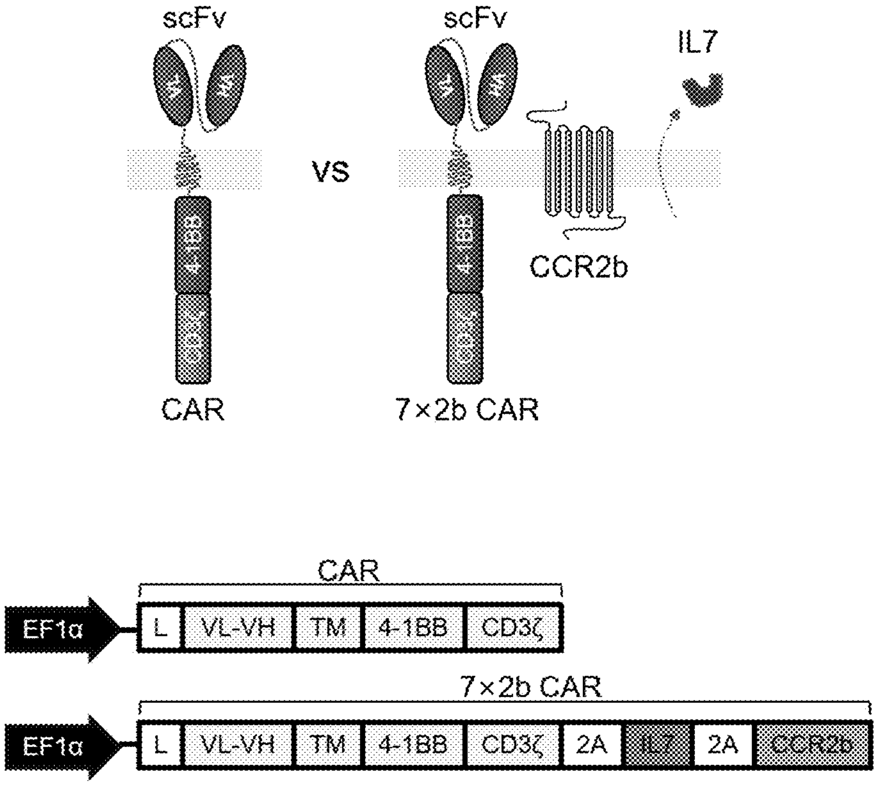
FIG. 1 shows a structural representation comparison between a conventional CAR and a CAR co-expressing IL-7 and CCR2b (7×2b) in an embodiment of the present disclosure.

Reference to the embodiments of the present disclosure will now be provided in detail, in which one or more examples are described below. Each example is provided for explaining but not intended to limit the present disclosure. Indeed, it would be apparent to those skilled in the art that various modifications and variations can be made to the present disclosure without departing from the scope or spirit of the present disclosure. For example, a feature stated or described as a part of one embodiment may be used in another embodiment to form a further embodiment.

Unless otherwise defined, all technical and scientific terms used herein have the same meaning as normally understood by those skilled in the art to which the present disclosure belongs. The terms used herein in the specification of the present disclosure are for the purpose of describing specific embodiments only and are not intended to limit the present disclosure. The term "and/or" as used herein includes any and all combinations of one or more related listed items.

The present disclosure relates to a fusion protein including a chimeric antigen receptor. The fusion protein includes a chimeric antigen receptor, a 2A peptide, IL-7, a 2A peptide and CCR2b which are sequentially linked in series.

Interleukin-7 (IL7) is a kind of multi-effect cytokines with broad immune effects, which can affect the growth, survival and differentiation of B cells and T cells, and also have direct or indirect effects on anti-tumor.

Chemokine receptor type 2 (CCR2) is a receptor of monocyte chemoattractant protein-1 (MCP-1). It has been confirmed that CCR2 and its ligand MCP-1 can play an important role in the pathology of inflammatory diseases, such as resistance to *Mycobacterium tuberculosis* during lung transplantation, lipopolysaccharide-induced death, delayed atopic dermatitis, etc.

In order to improve the therapeutic effect of CAR-T cell on a solid tumor, a CAR-T cell co-expressing IL-7 and CCR2b (7×2b CAR-T) is constructed and prepared in the present disclosure. The 7×2b CAR-T cell can have viability, chemotactic ability and subset distribution superior to those of the conventional CART cell, so that it is expected to achieve superior anti-tumor effects in vivo, and provide a preclinical research basis for future clinical trials.

In some embodiments, the IL-7 has an amino acid sequence as set forth in SEQ ID NO: 2.

In some embodiments, the IL-7 further includes a signal peptide. The signal peptide optionally has an amino acid sequence as set forth in SEQ ID NO: 9.

In some embodiments, the CCR2b has an amino acid sequence as set forth in SEQ ID NO: 3.

In some embodiments, the 2A peptide is a T2A peptide having an amino acid sequence as set forth in SEQ ID NO: 4.

In some embodiments, the chimeric antigen receptor includes A) a sc-Fv region, B) a hinge region, C) a transmembrane region, and D) an intracellular signaling region.

In some embodiments, the hinge region is a hinge region of CD8α. In an embodiment, the hinge region has an amino acid sequence as set forth in SEQ ID NO: 5.

In some embodiments, the transmembrane region is any one selected from α, β or ζ chain of a T cell receptor, CD28, CD3ε, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2RO, IL2Rγ, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the transmembrane region is a CD8α transmembrane region having an amino acid sequence as set forth in SEQ ID NO: 6.

In some embodiments, the intracellular signaling region is any one selected from CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a CD83-specific binding ligand, CDS, ICAM-1, GITR, BAFFR, HVEM (LIGHTR), SLAMF7, NKp80 (KLRF1), CD160, CD19, CD4, CD8α, CD8β, IL2RO, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1(CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, PKCθ, FcεRIγ, ZAP70 and CD3ζ, or a combination thereof.

In some embodiments, the intracellular signaling region is 4-1BB and CD3ζ.

In some embodiments, the 4-1BB has an amino acid sequence as set forth in SEQ ID NO: 7.

In some embodiments, the CD3ζ has an amino acid sequence as set forth in SEQ ID NO: 8.

In some embodiments, the chimeric antigen receptor has a N-terminal signal peptide. The signal peptide optionally is a CD8α signal peptide. Further, the signal peptide has an amino acid sequence as set forth in SEQ ID NO: 10.

In some embodiments, the sc-Fv region is configured to target a surface marker on a solid tumor.

The sc-Fv region can be a chimeric, humanized, or human antibody fragment, and is an antigen-binding domain capable of recognizing a tumor. In some embodiments, the antigen-binding domain capable of recognizing a tumor can recognize any one of the following antigens: α-fetoprotein (AFP), α-actinin-4, A3, A33 antibody-specific antigen, ART-4, B7, Ba 733, BAGE, BrE3 antigen, CA125, CAMEL, CAP-1, carbonic anhydrase IX, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD79b, CD80, CD83, CD95, CD126, CD132, CD133, CD138, CD147, CD154, CDC27, CDK-4/m, CDKN2A, CTLA4, CXCR4, CXCR7, CXCL12, HIF-1α, colon-specific antigen p (CSAp), CEA (CEACAM-5), CEACAM-6, c-Met, DAM, EGFR, EGFRvIII, EGP-1 (TROP-2), EGP-2, ELF2-M, Ep-CAM, fibroblast growth factor (FGF), Flt-1, Flt-3, a folate receptor, G250 antigen, GAGE, gp100, GRO-0, HLA-DR, HM1.24, human chorionic gonadotropin (HCG) and its subunits, HER2/neu, HMGB-1, hypoxic inducible factor-1 (HIF-1), HSP70-2M, HST-2, Ia, IGF-1R, IFN-γ, IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4 antigen, KS-1 antigen, KS1-4, Le-Y, LDR/FUT, macrophage migration inhibitory factor (MIF), MAGE, MAGE-3, MART1, MART-2, NY-ESO-1, TRAG-3, mCRP, MCP-1, MIP-1α, MIP-1β, MIF, MUC1β, MUC2, MUC3, MUC4, MUC5ac, MUC13, MUC16, MUM-1/2, MUM-3, NCA66, NCA95, NCA90, pancreatic mucin, PD1 receptor, placental growth factor, p53, PLAGL2, prostatic acid phosphatase, PSA, PRAME, PSMA, PlGF, ILGF, ILGF-1R, IL-6, IL-25, RSS, RANTES, T101, SAGE, 5100, survivin, survivin-2B, TAC, TAG-72, cytotactin, TRAIL receptor, TNF-α, Tn antigen, Thomsen-Friedenreich antigen, tumor necrosis antigen, VEGFR, ED-B fibronectin, WT-1, 17-1A antigen, complement factors C3, C3a, C3b, C5a, C5, an angiogenesis marker, bc1-2, bc1-6, Kras, an oncogene marker, and an oncogene product.

In some embodiments, the sc-Fv region targets GD2. In an embodiment, the sc-Fv region has an amino acid sequence as set forth in SEQ ID NO: 1.

The present disclosure also relates to an isolated nucleic acid expressing the fusion protein as described above. The nucleic acid can be DNA or RNA.

The present disclosure further relates to a vector including the nucleic acid as described above.

In some specific embodiments of the present disclosure, the vector can be selected from a retrovirus vector, an adenovirus, an adenovirus-associated virus, or a CRISPR/CAS plasmid.

In some specific embodiments of the present disclosure, the retrovirus vector is a lentiviral vector.

In some specific embodiments of the present disclosure, the CRISPR/CAS plasmid can be any one selected from CRISPR/CAS-1, CRISPR/CAS-5, CRISPR/CAS-7, CRISPR/CAS-9, CRISPR/CAS-2, CRISPR/CAS-3 and CRISPR/CAS-10.

The present disclosure also relates to a T cell including the nucleic acid as described above or the vector as described above.

In some specific embodiments of the present disclosure, the T cell is any one of a helper T cell, a cytotoxic T cell, a memory T cell, a regulatory T cell, MAIT cell and γδT cell.

The present disclosure further relates to a composition including the T cell as described above and a pharmaceutically acceptable carrier.

The present disclosure further relates to use of the T cell as described above or the composition as described above in the preparation of a medicament for preventing and/or treating a solid tumor.

In the present disclosure, the solid tumor includes a tumor formed from the lesion of any one of bone, bone junction, muscle, lung, trachea, heart, spleen, arteries, veins, capillaries, lymph nodes, lymph vessels, lymph fluid, oral cavity, pharynx, esophagus, stomach, duodenum, small intestine, colon, rectum, anus, appendix, liver, bile, pancreas, parotid gland, sublingual gland, kidney, ureter, bladder, urethra, ovary, fallopian tube, uterus, vagina, genitalia, scrotum, testicle, vas deferens, penis, eyes, ears, nose, tongue, skin, brain, brainstem, medulla oblongata, spinal cord, cerebrospinal fluid, nerves, thyroid gland, parathyroid gland, adrenal gland, pituitary gland, pineal gland, pancreas islet, thymus, gonadal gland, sublingual gland, or parotid gland. In particular, the tumors intended to be targeted include, for example, cholangiocarcinoma, breast cancer, cervical cancer, chronic lymphocytic leukemia, chronic myeloid leukemia, colorectal cancer, endometrial cancer, esophageal cancer, stomach cancer, head and neck cancer, Hodgkin's lymphoma, lung cancer, medullary thyroid cancer, non-Hodgkin's lymphoma, multiple myeloma, kidney cancer, ovarian cancer, pancreatic cancer, glioma, melanoma, liver cancer, prostate cancer, or urinary bladder cancer.

In some embodiments, the solid tumor is a tumor with a high CCL2 level.

In some embodiments, the solid tumor is neuroblastoma or melanoma.

The present disclosure has the following beneficial advantages.

The conventional CAR-T cell cannot survive long enough in vivo and can be affected by various immunosuppressive factors in the tumor microenvironment, resulting in poor infiltration ability to the tumor and weak proliferation ability in the tumor microenvironment. A CAR-T cell co-expressing IL-7 and CCR2b, which is referred to as 7×2b CAR T cell, is constructed in the present disclosure. The 7×2b CAR T cell can be more effectively migrated to a solid tumor and can be efficiently proliferated in a tumor region.

Compared with the conventional CAR-T cell, the expression of CAR on the T cell surface and the specificity and effectiveness of CAR-T in killing tumor cells would not be affected by the secretion of IL-7 and the expression of CCR2b. Moreover, in the culture process without exogenous addition of IL-7, the 7×2b CAR T cell can exhibit a better proliferation ability, which would facilitate its survival in vivo and thus improve its clinical activity.

The embodiments of the present disclosure will be described in details in in combination with examples below.

Example 1. Design of Chimeric Antigen Receptor

In this example, a GD2-targeting CAR was constructed by using the single chain antibody (scFv) of anti-GD2 antibody 14G2a as the antigen-binding domain, in combination with CD8α signal peptide, CD8α hinge region, CD8α transmembrane region, 4-1BB co-stimulatory domain and CD3 signaling domain, with a structural schematic diagram as shown in panel A of FIG. 1. In this example, a CAR co-expressing IL-7 and CCR2b (7×2b) was also constructed, with a structural schematic diagram as shown in panel B of FIG. 1.

The amino acid sequence of 14G2a-CAR is shown in SEQ ID NO: 11. The nucleotide sequence of 14G2a-CAR is shown in SEQ ID NO: 12.

The amino acid sequence of 14G2a-CAR-7×2b is shown in SEQ ID NO: 13. The nucleotide sequence of 14G2a-CAR-7×2b is shown in SEQ ID NO: 14.

Example 2. Construction of Vector Expressing Chimeric Antigen Receptor (1) The CAR gene was optimized according to the theoretical protein sequence of the CAR gene, so that it can be efficiently expressed in human cells. The CAR gene was synthesized after codon optimization and by whole gene synthesis by GUANGZHOU IGE BIOTECHNOLOGY LTD.

(2) The synthesized CAR gene and the empty vector pLVX-EF1-MCS were respectively double-digested with EcoRI and BamHI in a water bath at 37° C. for 30 minutes, then subjected to DNA electrophoresis by using 1.5% agarose gel. An agarose gel kit from Tiangen Biotech (Beijing) Co., Ltd was used for purification and recovery.

(3) The vector pLVX-EF1-MCS and the CAR gene were ligated.

The ligation system is shown in Table 1.

TABLE 1

| Component | Addition amount (μl) |
|---|---|
| vector pLVX-EF1-MCS | 2 (50 ng) |
| CAR gene | 10 (150 ng) |
| T4 DNA ligation buffer | 2 |
| T4 DNA ligase (NEB) | 1 |
| dd $H_2O$ | 5 |
| total | 20 |

The ligation reaction was conducted at 22° C. for 1 hour. The ligated product was directly transformed into *Escherichia coli* Stbl3 competent cells. 200 μl of the transformed products were seeded onto a LB plate containing ampicillin. The LB plate was placed upside-down in an incubator at 37° C. overnight. In the next morning, three single colonies were randomly selected for colony PCR identification The positive colonies were sent for sequencing.

Figure 2A:
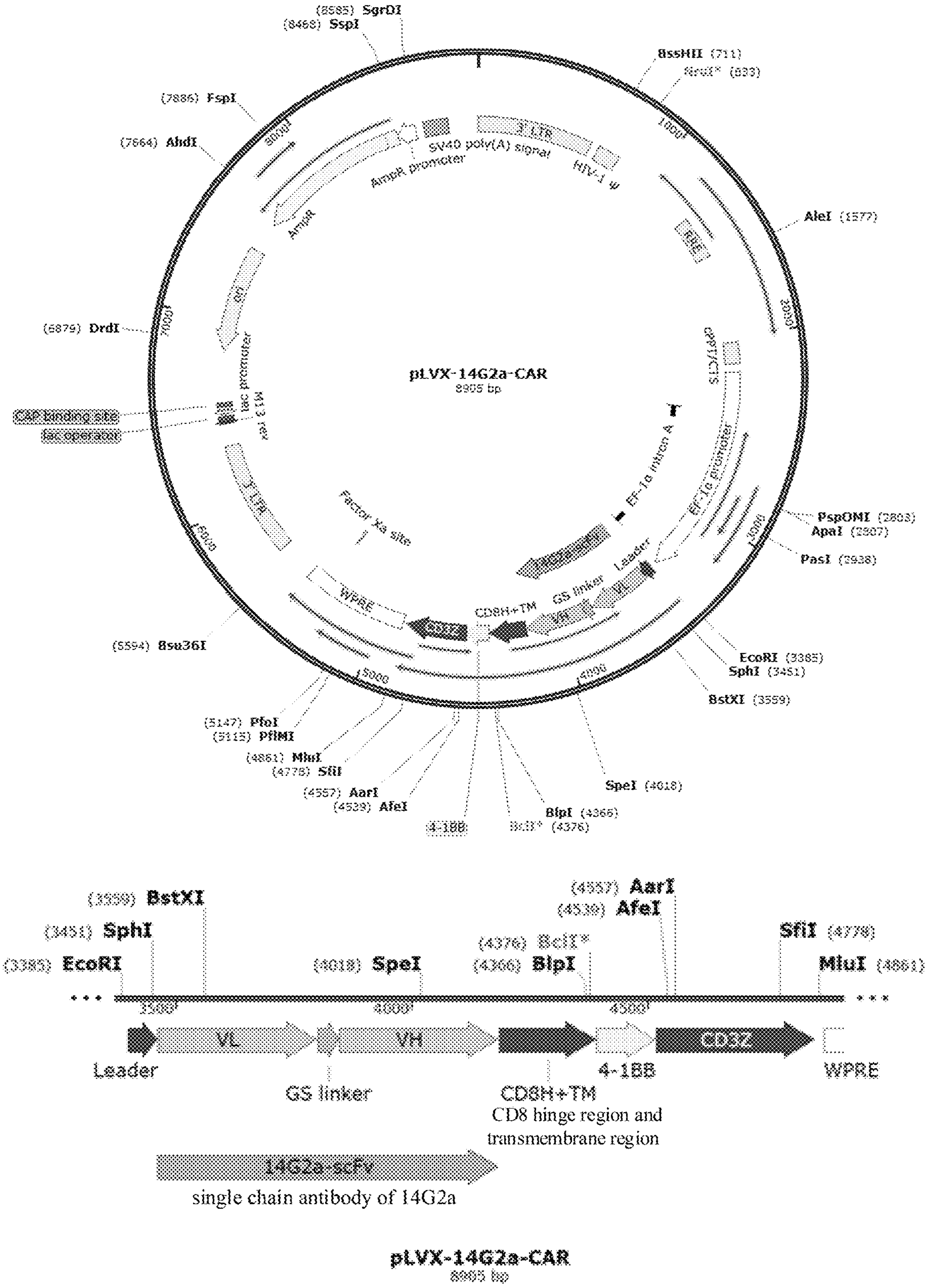
FIG. 2A shows the structure of a conventional CAR targeting GD2 in an embodiment of the present disclosure.
Figure 2B:
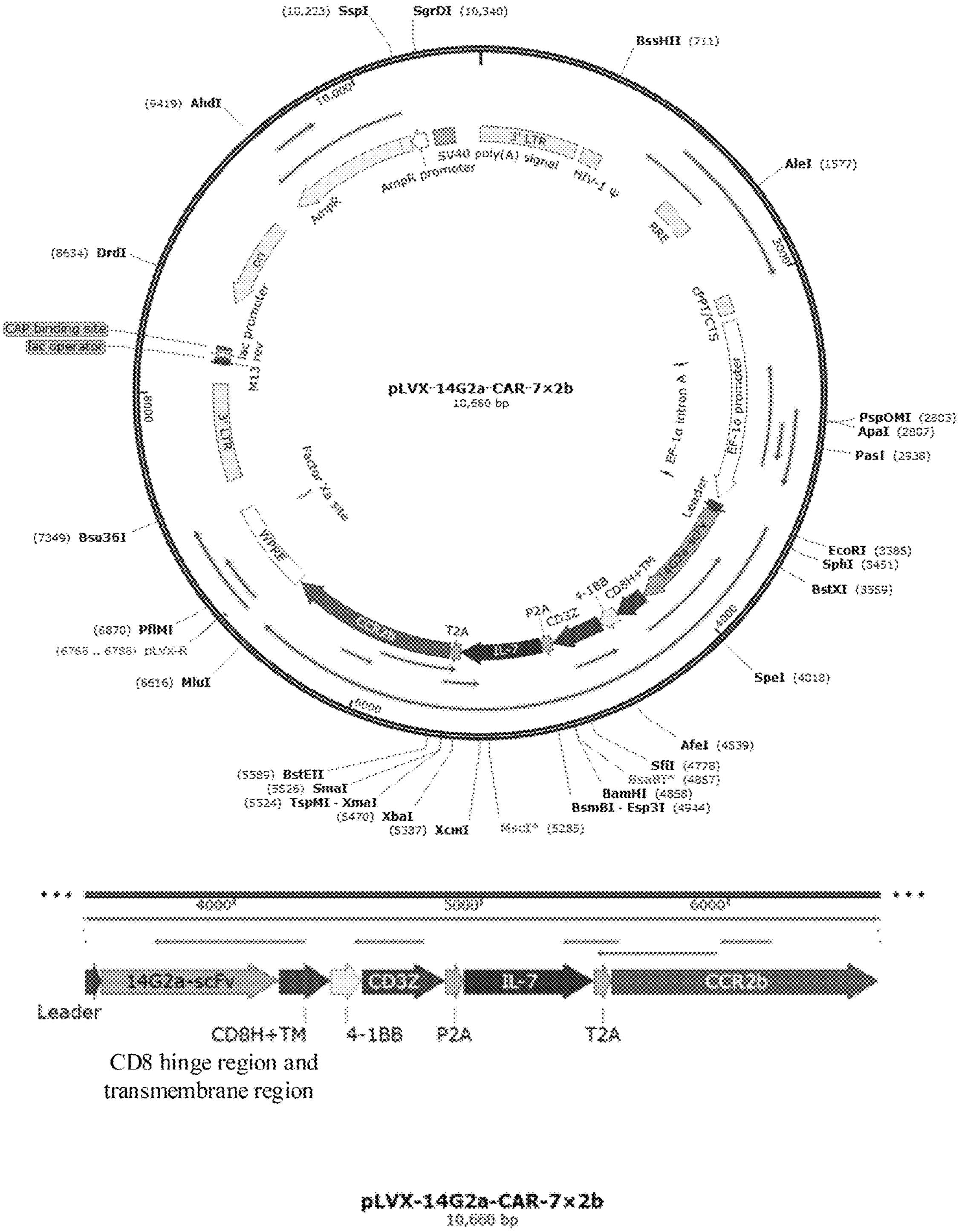
FIG. 2B shows the structure of a CAR co-expressing IL-7 and CCR2b (7×2b) in an embodiment of the present disclosure.

The vector map of the conventional chimeric antigen receptor lentiviral expression vector pLVX-14G2a-CAR is shown in FIG. 2A. The vector map of the chimeric antigen receptor lentiviral expression vector pLVX-14G2a-CAR-7×2b co-expressing IL-7 and CCR2b (7×2b) is shown in FIG. 2B.

Example 3. Package of Lentivirus

The lentiviral expression vectors obtained in Example 2 were packaged respectively with a four-plasmid system according to the following steps.

(1) The four-plasmid system expresses gag/pol, Rev, VSV-G and the CAR expression vector constructed in the present disclosure which are required for packaging lentivirus respectively. The four plasmids were used for transient transfection of 293 T cells, with a DNA content of 2 μg/mL.

(2) The above plasmids were mixed with a PEI transfection reagent and the mixture was added to a certain volume of serum-free Dulbecco's modified Eagle medium (DMEM). The mixture was mixed uniformly and allowed to stand for 15 minutes, and then added to a T75 culture bottle seeded with 293T cells, gently mixed, and cultured in a cell incubator containing 5% $CO_2$ at 37° C. for 6 hours.

(3) After 6 hours, the culture medium was replaced with a fresh medium for continuous culture. 10 mM of butyric acid sodium solution was added. After 72 hours, the supernatant of the cultured lentivirus was collected and purified for detecting.

Example 4. Preparation and Identification of CAR-T Cell

Peripheral blood mononuclear cells (PBMCs) were extracted from peripheral blood of a healthy human by using peripheral blood lymphocyte separation solution Ficoll. Human T cells were isolated with α-CD3/α-CD28 antibody-coated magnetic beads at a ratio of T cells to magnetic beads of 1:1, and then cultured in GT-T551 H3 Culture medium (Takara) containing 10% serum and 100 μg/mL IL-2. After 24 hours, activated human CD3+ T cells were counted. $0.1\times10^6$ T cells and the virus concentrate at a multiplicity of infection (MOI) of 10 were added into each well, and then placed in a cell incubator. The culture medium was changed with a fresh culture medium after 4 hours. Then, the fresh culture medium was supplemented every 2 to 3 days. The prepared CAR-T cells are designate as conventional CART cells and 7×2b CAR T cells, respectively. The non-infected human T cells (Mock T) were used as a negative control.

After 5 days of transduction, the T cells were washed with a flow cytometry wash solution made of 50 mL PBS and 1 mL fetal bovine serum, and then centrifuged. The cell precipitates were resuspended with 100 μL of FITC-labeled protein L or anti-CCR2b, each with a working concentration of 3 μg/mL, then incubated at 4° C. for 60 minutes. After that, the cells were washed with a flow cytometry wash solution for 3 times. The expressions of CAR and CCR2b on the surface of T cells were detected by flow cytometry. The supernatant was detected for the secretion level of IL-7. According to the requirements of Cytokine ELISA detection kit (i.e., Human IL-7 ELISA KIT), the secretion level of human IL-7 cytokine by CAR-T cells was detected by the double antibody sandwich method. The chromogenic substrate was developed, and then OD values at 450 nm were obtained using a microplate reader. The corresponding concentrations of cytokine in each sample were calculated according to a standard curve.

Figure 3:
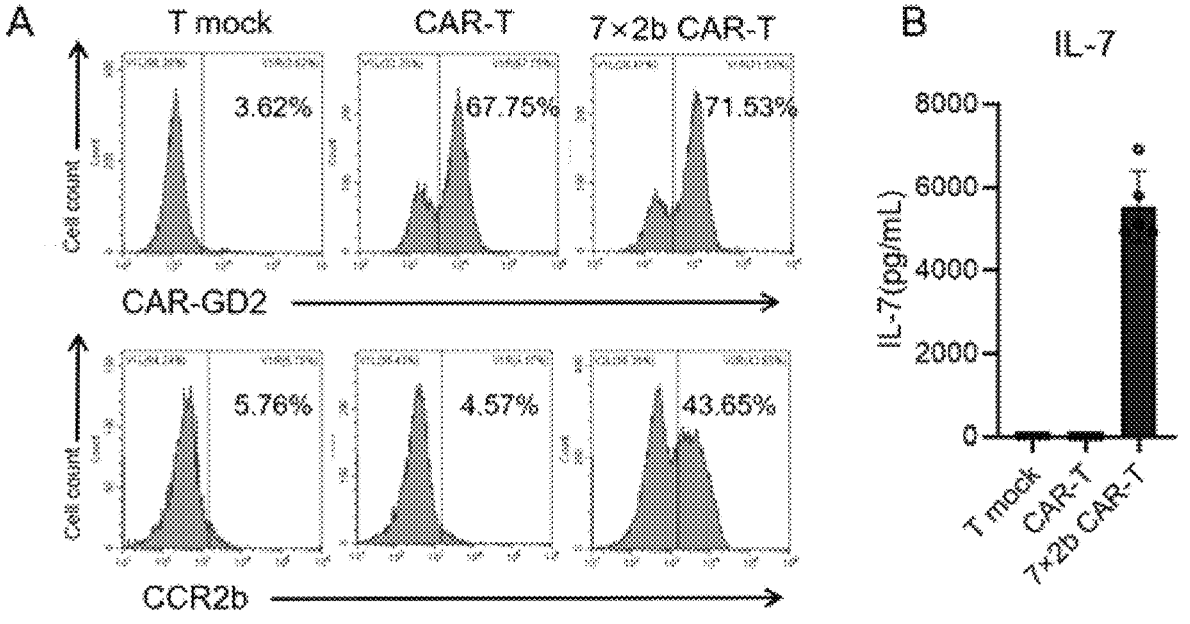
FIG. 3 shows the expression of CAR-T detected by flow cytometry and the secretion of IL-7 detected by ELISA in an embodiment of the present disclosure.
Figure 4:
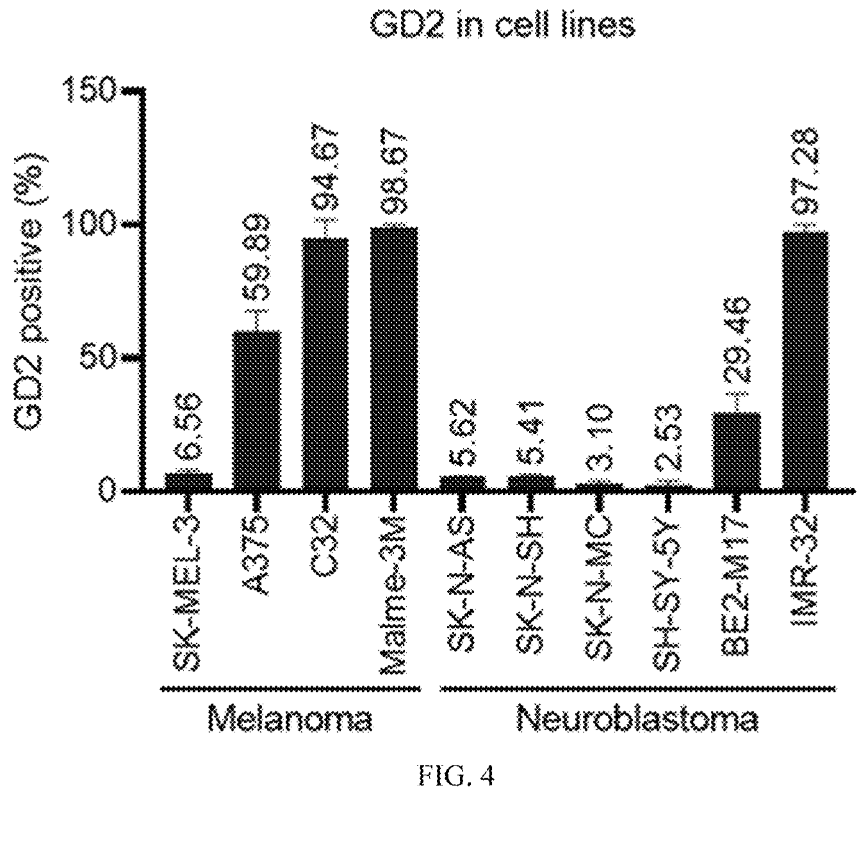
FIG. 4 shows the expression of GD2 antigen in melanoma and neuroblastoma detected by flow cytometry in an embodiment of the present disclosure.

To further verify whether the 7×2b CART cell can express CCR2b and effectively secrete IL-7, FITC-protein L (1:100) was used to detect the expression of CAR, and APC anti-human CD192 (CCR2) antibody (biolegend; 1:20) was used to detect the expression of CCR2b. It is shown that the expression of CAR detected by the protein L is 3.62% for Mock T, 67.75% for the conventional 14G2a-CAR-T, and 71.53% for the 7×2b CAR-T co-expressing IL-7 and CCR2b. In addition to CAR, the 7×2b CAR-T cell can also express CCR2b, referring to panel A of FIG. 3. The T cells were cultured in H3 medium without IL-7. The culture supernatant of T cells was taken on Day 5 for detecting the concentration of IL-7 in the supernatant by the ELISA method. It is shown that the 7×2b CAR-T cells can secrete a large amount of IL-7, but IL-7 secretion is undetectable in the control T cells without transduction of lentivirus (i.e., Mock T) or in the CAR-T cells transduced with only the conventional CAR structure, referring to panel B of FIG. 3.

Example 5. Determination of In Vitro Anti-Tumor Activity of CAR-T Cell

It has been reported previously that the GD2 antigen can be expressed in melanoma and neuroblastoma. The expression of GD2 in the cell lines was detected by using anti-Ganglioside GD2 antibody [14.G2a] (ab68456) in this Example. As shown in FIG. 2A, in the melanoma cell lines, the GD2 antigen is highly expressed in the cell lines other than SK-MEL3 cell line; while in the neuroblastoma cell lines, the GD2 antigen is lowly expressed in the cell lines other than BE2-M17 and IMR-32 cell lines.

Figure 5:
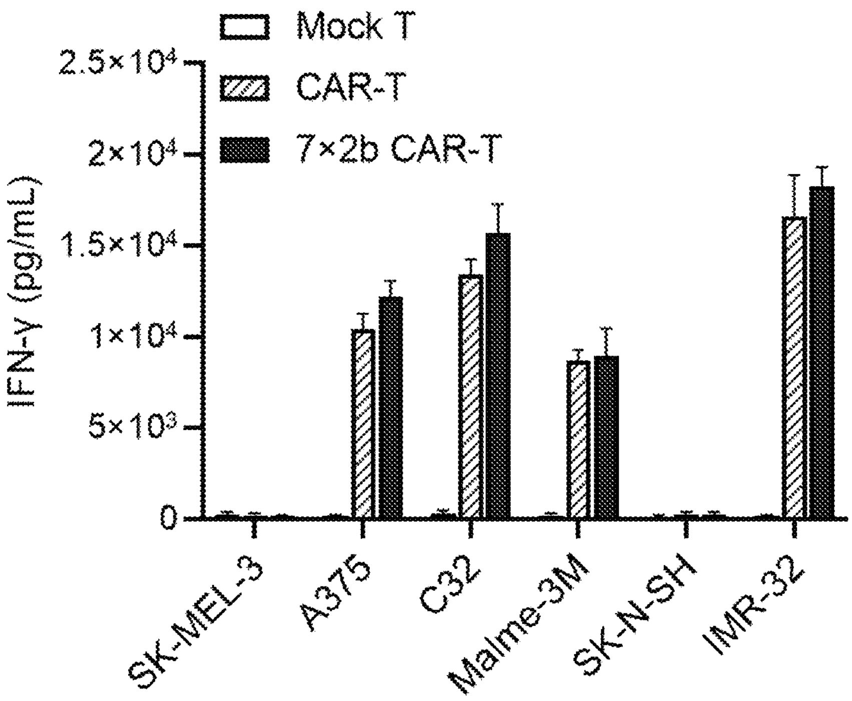
FIG. 5 shows the secretion levels of IFN-γ by the CAR-T cell after co-incubation with tumor cells detected by ELISA in an embodiment of the present disclosure.

The non-transduced control T cells, classic CART cells and 7×2b CAR-T cells were co-cultured with different GD2-expressing tumor cells, respectively. The effector-target (E/T) ratio of CAR-T cells to target tumor cells is 10:1. After co-incubation in a 96-well plate for 12 hours, IFN-γ level in the supernatant was detected using an ELISA kit. In both the conventional CAR-T cell group and the 7×2b CAR-T cell group, a large amount of IFN-γ was secreted after co-incubation with the GD2-positive tumor cells, while almost no IFN-γ was secreted after co-incubation with the GD2-negative tumor cells, as shown in FIG. 5, indicating that the 7×2b CAR-T cell group and conventional CAR-T cell group can be specifically activated by the GD2-expressing tumor cells, and thus can secrete inflammatory cytokine IFN-γ, and produce immunotoxicity effects on the GD2-positive tumor cells. In addition, after co-incubation with the GD2-positive tumor cells, the secretion level of IFN-γ in the 7×2b CAR-T cell group is higher than that in the conventional CAR-T cell group, with not statistically significant difference.

Figure 6:
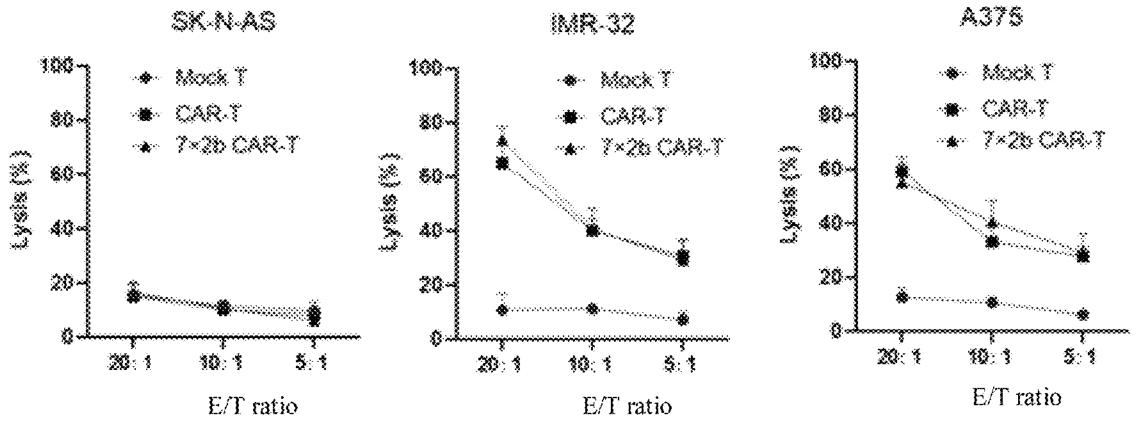
FIG. 6 shows the killing efficiency of the CAR-T cell detected by luciferase assay in an embodiment of the present disclosure.

The killing rates (%) to the three tumor cell lines by CAR-T cells at different effector-target ratios were determined by a luciferase assay. SK-N-AS cells, IMR-32 cells and A375 cells are previously transduced with the luciferase gene respectively to construct cell lines stably expressing luciferase. The T cells in each group were incubated with the three target tumor cells at different E/T ratios for 4 hours. It is shown that there is no significant difference in the killing effects between the 7×2b CAR-T cell group and the conventional CAR-T cell group. The CAR-T cells can kill the GD2-positive IMR-32 cells and A375 cells, but cannot kill the GD2-negative SK-N-AS cells, exhibiting a good specificity (FIG. 6).

Figure 7:
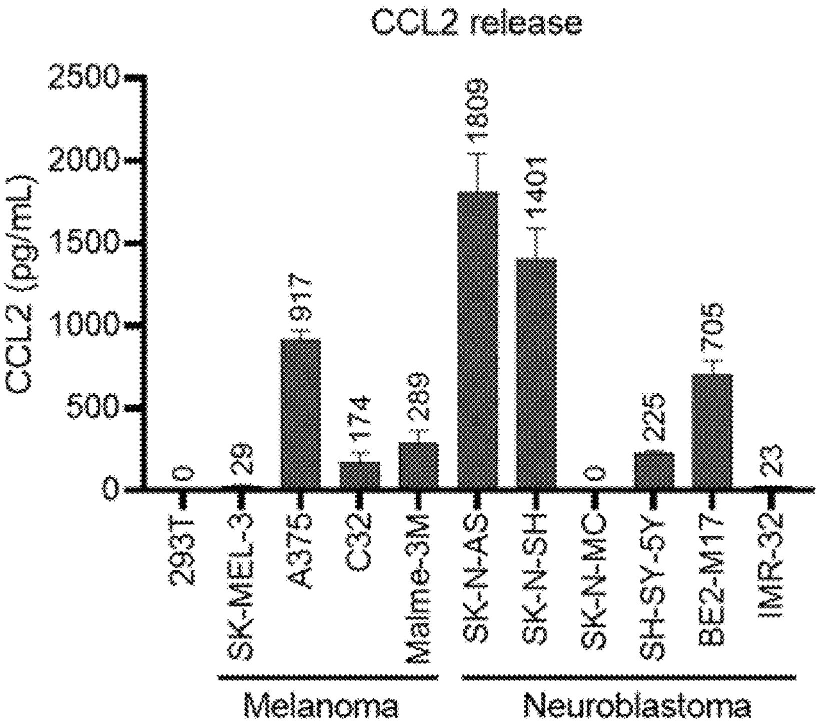
FIG. 7 shows the secretion levels of CCL2 by tumor cells detected by ELISA in an embodiment of the present disclosure.

Example 6. Enhanced Survival and Migration Ability of CAR-T Cells by the Expression of IL-7 and CCR2b C—C motif Chemokine ligand 2 (CCL2), secreted by various tumor cells, is a member of the chemokine family that is earliest discovered and widely researched, and has a strong chemotaxis to mononuclear cells, memory T cells, and the like. Therefore, CCR2b, as a CCL2 receptor, is introduced into the structure of CAR to improve the chemotaxis of the CAR-T cells. The secretion levels of CCL2 by tumor cells were detected by the ELISA method. The results are shown in FIG. 7.

It is shown that almost no CCL2 is secreted by 293T, SK-MEL-3, SK-N-MC or IMR-32 cells; CCL2 is slightly secreted by C32, Malme-3M or SH-SY-5Y cells; and CCL2 is largely secreted by A375, SK-NS-AS, SK-N-SH or BE2M17 cells. The SK-NS-AS cells secreted the largest amount of CCL2.

Figure 8:
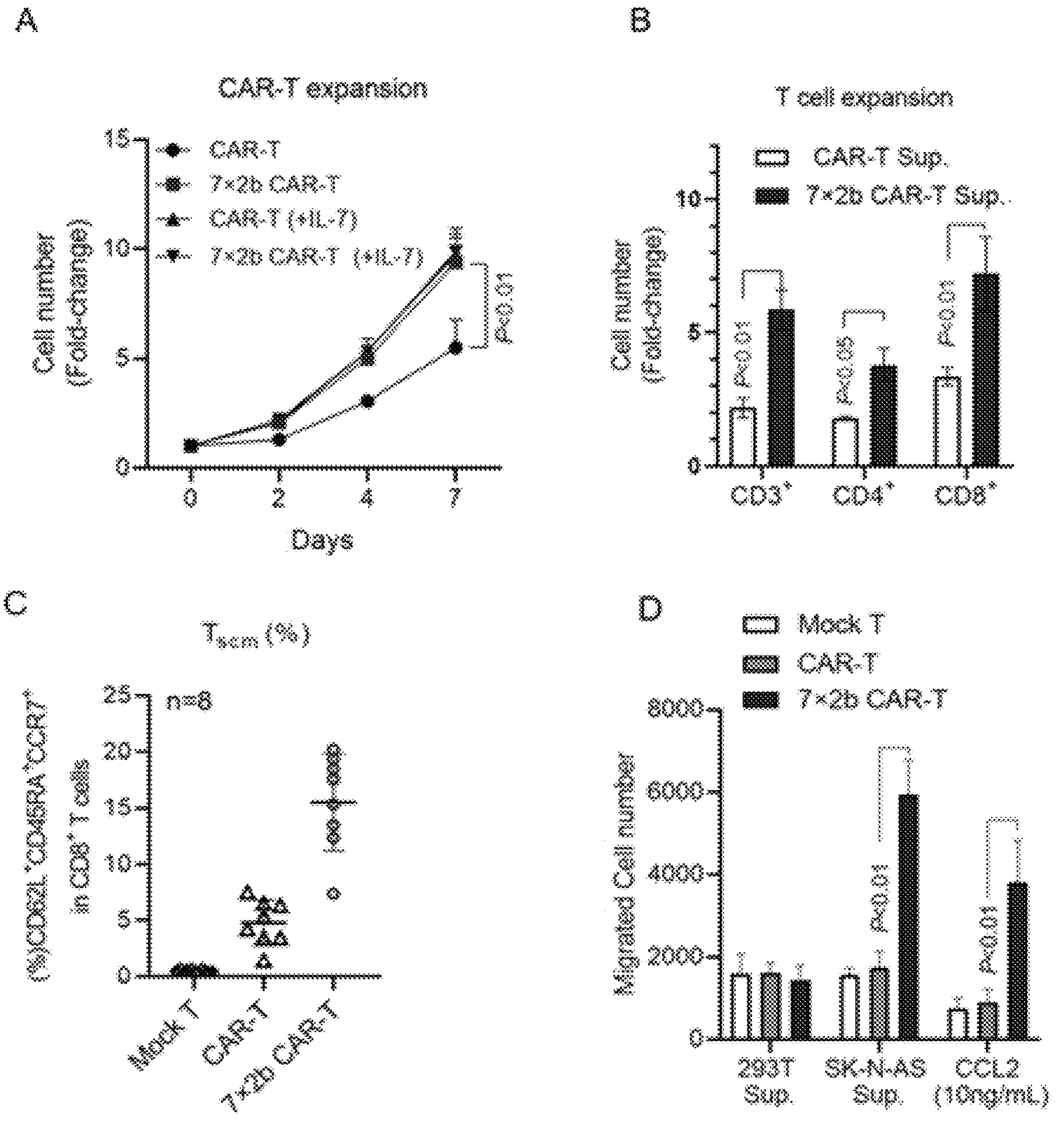
FIG. 8 shows the effect of the CAR-T cell on promoting proliferation and migration in an embodiment of the present disclosure, in which (A) shows evaluation of the expansion efficiency of the CAR-T cell; (B) shows effect of the CAR-T cell supernatant on stimulating T cell expansion; (C) shows analysis of Tscm subset; and (D) shows evaluation of the chemotactic ability of the tumor cell supernatant to the CAR-T cell.

Cytokine IL-7 can effectively promote the proliferation of T cells. In order to further validate the function of the 7×2b CAR-T cells, the proliferation ability of CAR-T cells is first tested. As shown in panel A of FIG. 8, from Day 2 after antigen activation, the 7×2b CAR-T cells has proliferation ability significantly superior to that of the conventional CAR-T cells. When cultured under the addition of 10 ng/mL of IL-7, the expansion ability of the conventional CAR-T cells is improved, indicating that IL7 can enhance the expansion of the CAR-T cells. However, there was no change in cell proliferation of the 7×2b CAR-T cells when cultured under the addition of IL7, indicating that the IL7 secreted by the 7×2b CAR-T cells is sufficient to satisfy the demand for expansion.

The effect of CAR-T cell supernatant on stimulating the expansion of T cells was further analyzed. The supernatant of conventional CAR-T cells or 7×2b CAR-T cells after culture was collected and then mixed with a fresh medium (TAKARA GT-T551 H3 serum-free medium+2% autologous serum+300 U/mL IL2) at a ratio of 1:1. T cells derived from PBMC in a concentration of $1\times10^6$ were added with the mixed culture medium, and the above mixed culture medium was supplemented every 2 to 3 days. After continuous culture for 7 days, the expansion ratios of CD3+, CD4+ and CD8+ subsets of T cells were detected by the flow cytometry. It is shown that T cells can be expanded by the supernatant in both the conventional CAR-T group and the 7×2b CAR-T group, and the numbers of CD3+, CD4+ and CD8+ T cells expanded in the 7×2b CAR-T group is more than those in the conventional CAR-T group, with the largest expansion number for CD8+ T cells, as shown in panel B of FIG. 8.

Since T cell subsets play an important role in the efficacy of CAR-T immunotherapy, the above three groups of T cells were cultured independently for 8 times, and then the distributions of T cell subsets were compared by the flow cytometry. It is shown that in the 7×2b CAR-T group, the proportion of T memory stem cells (Tscm) ($CAR^+CD62L^+CD45RA^+CCR7^+$) in CD8+ T cells is significantly higher than that in Mock T cell group and the conventional CAR-T cell group, with statistically significant difference ($P<0.001$), indicating that the 7×2b CAR-T cells have good persistence, as shown in panel C of FIG. 8.

The chemotactic ability of CCL2 in the supernatant of tumor cells to CAR-T cells was further evaluated. The SK-N-AS cell, which can secrete the largest amount of CCL2, was selected as the research object, and 293 T cell was used as a negative control. After the cells with a concentration of $5\times10^6$ cells per well were cultured in a serum free medium for 48 hours, the supernatant was collected and added in the lower chamber of Transwell. Among them, one group with 10 ng/mL of CCL2 added in the serum-free medium was served as a positive control. $3\times10^4$ of Mock T cells, conventional CAR-T cells or 7×2b CAR-T cells were respectively added in the upper chambers of Transwell and cultured for 24 hours. Then the T cells migrated into the lower chambers were counted by the flow cytometry. It is shown that the supernatant of 293 T cells can facilitate a small number of the T cells to migrate into the lower chambers, but there is no significant difference in the migrated numbers of the T cells. However, in the wells with addition of the SK-N-AS cell supernatant, the number of the 7×2b CAR-T cells migrated into the lower chamber is larger than that of Mock T cells and the conventional CAR-T cells, with statistically significant difference ($P<0.01$). The addition of 10 ng/mL CCL2 in the lower chamber can also cause a substantial migration of T cells, as shown in panel D of FIG. 8. It is suggested that the CCR2b receptor in the 7×2b CAR T cells can be induced by CCL2 secreted by SK-N-AS cells, which promotes the chemotaxis of the 7×2b CAR-T cells towards the supernatant containing CCL2.

Example 7. In Vivo Anti-Tumor Activity of 7×2b CAR-T Cells

Figure 9:
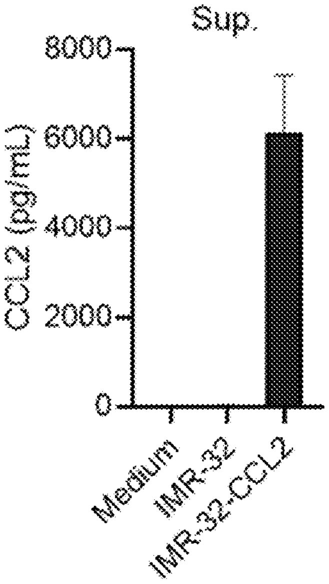
FIG. 9 shows secretion level of CLL2 by the IMR-32-CCL2 cell stably transfected with CLL2 gene detected by ELISA in an embodiment of the present disclosure.

The 7×2b CAR-T cells were further studied for inhibiting tumors in vivo. IMR-32 cell, which scarcely secretes CCL2, was selected as the research object. A stably transfected cell line IMR-32-CCL2 was constructed to express CCL2 gene and a luciferase marker. As shown in FIG. 9, a high concentration of CCL2 is detected in the culture supernatant of IMR-32-CCL2 cells by the ELISA method, indicating that the stably transfected cell line constructed can secrete CCL2, and the construction is successful.

Figure 10:
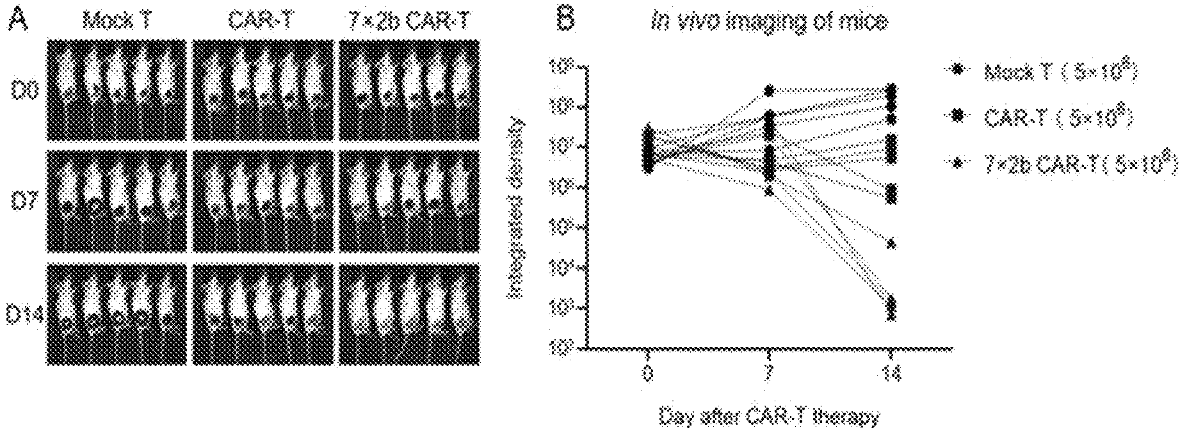
FIG. 10 shows an in vivo imaging of the mice and analysis data of the bioluminescence imaging results.

The stably transfected cell line IMR-32-CCL2 was injected subcutaneously into nude mice, with a concentration of $5\times10^6$ cells per mouse, to form a tumor. After 10 days, the mice were divided into a Mock T group, a CAR-T group and a 7×2b CAR-T group, with 5 nude mice in each group. The Mock T cells, conventional CAR-T cells and 7×2b CAR-T cells were re-infused into the nude mice via the tail vein, with a concentration of $5\times10^6$ cells per mouse. The nude mice were imaged in vivo on Day 0, Day 7 and Day 14. The bioluminescence imaging results are as shown in panel A of FIG. 10. Compared with the Mock T group or the conventional CAR-T group, the 7×2b CAR-T cells can effectively inhibit tumor growth, and cause regression of the tumor in mice on Day 14. The corresponding quantitative analysis of fluorescence intensity is shown in panel B of FIG. 10.

Figure 11:
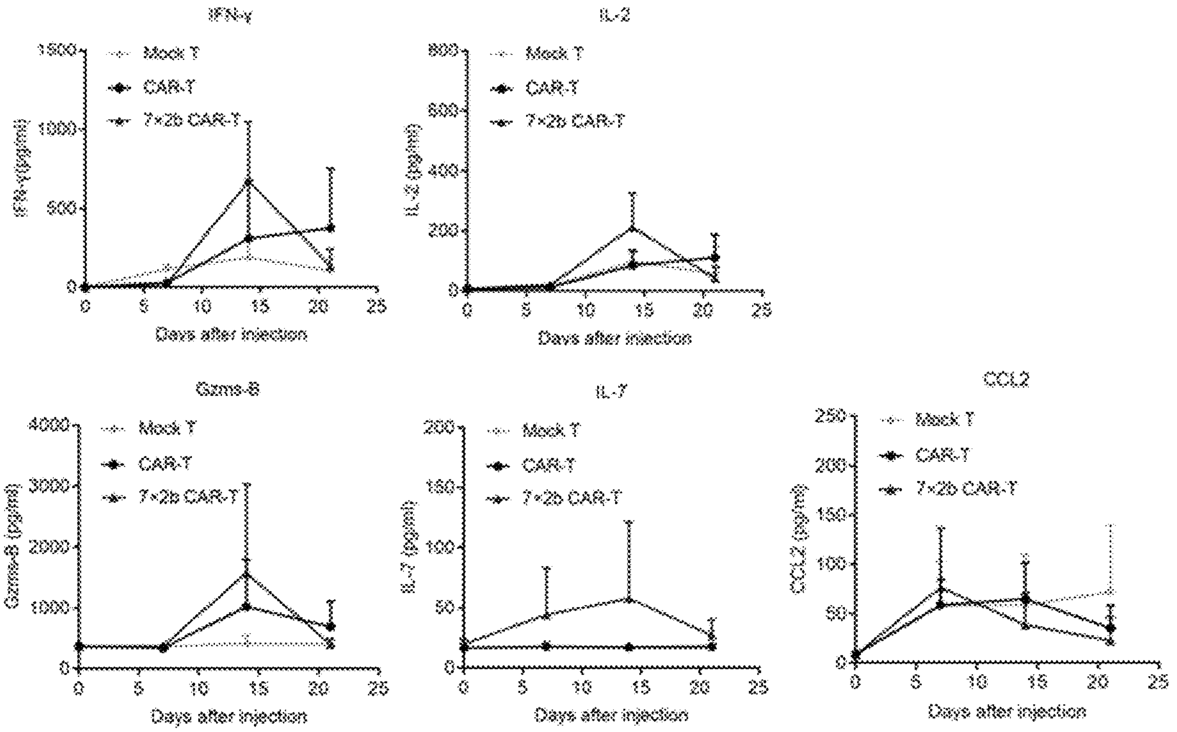
FIG. 11 shows secretion levels of cytokines by mice after being treated with CAR-T in an embodiment of the present disclosure.

In addition, the tail venous bloods of the nude mice in each group were collected for detecting the contents of various human cytokines by the flow cytometry-based BCA method. As shown in FIG. 11, the expressions of IFN-γ, IL2 and Gzms-B are all increased on day 14 after re-infusion of the 7×2b CAR-T cells, indicating that the 7×2b CAR-T cells have the tumor-killing effect. IL-7 can be only found in the venous bloods of the mice in the 7×2b CAR-T group, indicating that IL-7 is secreted by the 7×2b CAR-T cells. CCL2 is detectable in the venous bloods of the mice in each group, with no significant difference in the level of CCL2, suggesting that CCL-2 is secreted by the inoculated IMR-32-CCL2 cells.

Figure 12:
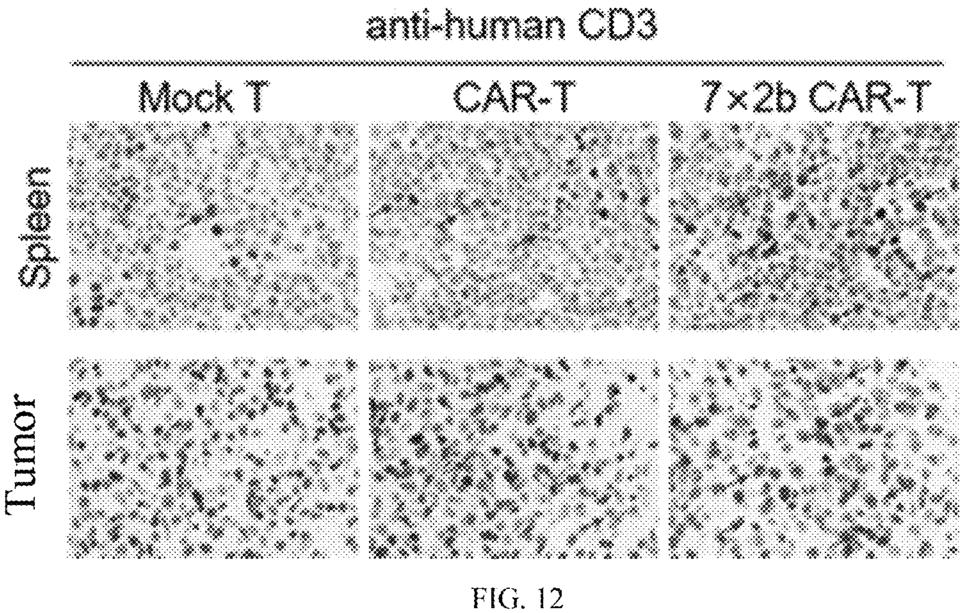
FIG. 12 shows expression of human CD3 in the spleen and tumor mass of mice detected by immunohistochemical tests in an embodiment of the present disclosure.

The expression of human CD3 can reflect the number of T cells re-infused in the spleen of the mice and the infiltration extent in the tumor. On day 7, the spleen and the tumor mass of the nude mice were respectively taken for immunohistochemical tests. The results show that the largest number of the 7×2b CAR-T cells exist in the spleen, as shown in FIG. 12, indicating that the 7×2b CAR-T cells have a strong expansion ability, and are more prone to migrate to a tumor site than the Mock T cells and the CAR T cells.

The technical features of the above-mentioned embodiments can be combined arbitrarily. In order to make the description concise, not all possible combinations of the technical features are described in the embodiments. However, as long as there is no contradiction in the combination of these technical features, the combinations should be considered as in the scope of the present disclosure.

The above-described embodiments are only several implementations of the present disclosure, and the descriptions are relatively specific and detailed, but they should not be construed as limiting the scope of the present disclosure. It should be understood by those of ordinary skill in the art that various modifications and improvements can be made without departing from the concept of the present disclosure, and all of them fall within the protection scope of the present disclosure. Therefore, the protection of the present disclosure shall be defined by the appended claims.

What is claimed is:

1. A fusion protein comprising a chimeric antigen receptor, wherein the fusion protein comprises a chimeric antigen receptor, a 2A peptide, IL-7, a 2A peptide and CCR2b which are sequentially linked in series,
 wherein the IL-7 comprises an amino acid sequence as set forth in SEQ ID NO: 2;
 the CCR2b comprises an amino acid sequence as set forth in SEQ ID NO: 3;
 the chimeric antigen receptor comprises A) a sc-Fv region, B) a hinge region, C) a transmembrane region, and D) an intracellular signaling region;
 the hinge region is a hinge region of CD8α,
 the transmembrane region is a CD8α transmembrane region,
 the intracellular signaling region is 4-1BB and CD3ζ, and
 the sc-Fv region is configured to target GD2 on a solid tumor.

2. The fusion protein according to claim 1, wherein the 2A peptide is a T2A peptide comprising an amino acid sequence as set forth in SEQ ID NO: 4.

3. The fusion protein according to claim 1, wherein the hinge region comprises an amino acid sequence as set forth in SEQ ID NO: 5.

4. The fusion protein according to claim 1, wherein the transmembrane region comprises an amino acid sequence as set forth in SEQ ID NO: 6.

5. The fusion protein according to claim 1, wherein the 4-1BB comprises an amino acid sequence as set forth in SEQ ID NO: 7, and the CD3ζ comprises an amino acid sequence as set forth in SEQ ID NO: 8.

6. The fusion protein according to claim 1, wherein the sc-Fv region comprises an amino acid sequence as set forth in SEQ ID NO: 1.

7. A T cell expressing the fusion protein of claim 1.

8. A composition comprising the T cell of claim 7 and a pharmaceutically acceptable carrier.

9. A method for preventing and/or treating a solid tumor, comprising administering a T cell expressing the fusion protein of claim 1 or a composition comprising the T cell to a subject in need thereof.

* * * * *

SEQUENCE LISTING

```
<160> NUMBER OF SEQ ID NOS: 14

<210> SEQ ID NO 1
<211> LENGTH: 241
<212> TYPE: PRT
<213> ORGANISM: Artificial Sequence
<220> FEATURE:
<223> OTHER INFORMATION: amino acid sequence of sc-Fv region

<400> SEQUENCE: 1

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Glu Val Gln Leu Leu Gln Ser Gly Pro Glu Leu Glu Lys Pro Ser Ala
    130                 135                 140

Ser Val Met Ile Ser Cys Lys Ala Ser Gly Ser Ser Phe Thr Gly Tyr
```

```
145                 150                 155                 160

Asn Met Asn Trp Val Arg Gln Asn Ile Gly Lys Ser Leu Glu Trp Ile
                165                 170                 175

Gly Ala Ile Asp Pro Tyr Tyr Gly Gly Thr Ser Tyr Asn Gln Lys Phe
            180                 185                 190

Lys Gly Arg Ala Thr Leu Thr Val Asp Lys Ser Ser Ser Thr Ala Tyr
        195                 200                 205

Met His Leu Lys Ser Leu Thr Ser Glu Asp Ser Ala Val Tyr Tyr Cys
    210                 215                 220

Val Ser Gly Met Glu Tyr Trp Gly Gln Gly Thr Ser Val Thr Val Ser
225                 230                 235                 240

Ser


<210> SEQ ID NO 2
<211> LENGTH: 152
<212> TYPE: PRT
<213> ORGANISM: Artificial Sequence
<220> FEATURE:
<223> OTHER INFORMATION: amino acid sequence of IL-7

<400> SEQUENCE: 2

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150


<210> SEQ ID NO 3
<211> LENGTH: 360
<212> TYPE: PRT
<213> ORGANISM: Artificial Sequence
<220> FEATURE:
<223> OTHER INFORMATION: amino acid sequence of CCR2b

<400> SEQUENCE: 3

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
```

```
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
            340                 345                 350

Glu Gln Glu Val Ser Ala Gly Leu
        355                 360


<210> SEQ ID NO 4
<211> LENGTH: 21
<212> TYPE: PRT
<213> ORGANISM: Artificial Sequence
<220> FEATURE:
<223> OTHER INFORMATION: amino acid sequence of T2A peptide

<400> SEQUENCE: 4

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 5
<211> LENGTH: 45
<212> TYPE: PRT
```

<213> ORGANISM: Artificial Sequence
<220> FEATURE:
<223> OTHER INFORMATION: amino acid sequence of CD8-alpha hinge region

<400> SEQUENCE: 5

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 6
<211> LENGTH: 24
<212> TYPE: PRT
<213> ORGANISM: Artificial Sequence
<220> FEATURE:
<223> OTHER INFORMATION: amino acid sequence of CD8-alpha transmembrane region

<400> SEQUENCE: 6

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 7
<211> LENGTH: 42
<212> TYPE: PRT
<213> ORGANISM: Artificial Sequence
<220> FEATURE:
<223> OTHER INFORMATION: amino acid sequence of 4-1BB

<400> SEQUENCE: 7

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 8
<211> LENGTH: 112
<212> TYPE: PRT
<213> ORGANISM: Artificial Sequence
<220> FEATURE:
<223> OTHER INFORMATION: amino acid sequence of CD3-zeta

<400> SEQUENCE: 8

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95
```

Thr Lys Asp Thr Tyr Asp Ala Leu His Met Gln Ala Leu Pro Pro Arg
100 105 110

<210> SEQ ID NO 9
<211> LENGTH: 25
<212> TYPE: PRT
<213> ORGANISM: Artificial Sequence
<220> FEATURE:
<223> OTHER INFORMATION: amino acid sequence of signal peptide

<400> SEQUENCE: 9

Met Phe His Val Ser Phe Arg Tyr Ile Phe Gly Leu Pro Pro Leu Ile
1 5 10 15

Leu Val Leu Leu Pro Val Ala Ser Ser
20 25

<210> SEQ ID NO 10
<211> LENGTH: 21
<212> TYPE: PRT
<213> ORGANISM: Artificial Sequence
<220> FEATURE:
<223> OTHER INFORMATION: amino acid sequence of CD8-alpha signal peptide

<400> SEQUENCE: 10

Met Ala Leu Pro Val Thr Ala Leu Leu Leu Pro Leu Ala Leu Leu Leu
1 5 10 15

His Ala Ala Arg Pro
20

<210> SEQ ID NO 11
<211> LENGTH: 485
<212> TYPE: PRT
<213> ORGANISM: Artificial Sequence
<220> FEATURE:
<223> OTHER INFORMATION: amino acid sequence of 14G2a-CAR

<400> SEQUENCE: 11

Met Ala Leu Pro Val Thr Ala Leu Leu Leu Pro Leu Ala Leu Leu Leu
1 5 10 15

His Ala Ala Arg Pro Asp Val Val Met Thr Gln Thr Pro Leu Ser Leu
20 25 30

Pro Val Ser Leu Gly Asp Gln Ala Ser Ile Ser Cys Arg Ser Ser Gln
35 40 45

Ser Leu Val His Arg Asn Gly Asn Thr Tyr Leu His Trp Tyr Leu Gln
50 55 60

Lys Pro Gly Gln Ser Pro Lys Leu Leu Ile His Lys Val Ser Asn Arg
65 70 75 80

Phe Ser Gly Val Pro Asp Arg Phe Ser Gly Ser Gly Ser Gly Thr Asp
85 90 95

Phe Thr Leu Lys Ile Ser Arg Val Glu Ala Glu Asp Leu Gly Val Tyr
100 105 110

Phe Cys Ser Gln Ser Thr His Val Pro Pro Leu Thr Phe Gly Ala Gly
115 120 125

Thr Lys Leu Glu Leu Lys Gly Gly Gly Gly Ser Gly Gly Gly Gly Ser
130 135 140

Gly Gly Gly Gly Ser Glu Val Gln Leu Leu Gln Ser Gly Pro Glu Leu
145 150 155 160

Glu Lys Pro Ser Ala Ser Val Met Ile Ser Cys Lys Ala Ser Gly Ser
165 170 175

Ser Phe Thr Gly Tyr Asn Met Asn Trp Val Arg Gln Asn Ile Gly Lys

```
            180                 185                 190

Ser Leu Glu Trp Ile Gly Ala Ile Asp Pro Tyr Tyr Gly Gly Thr Ser
        195                 200                 205

Tyr Asn Gln Lys Phe Lys Gly Arg Ala Thr Leu Thr Val Asp Lys Ser
    210                 215                 220

Ser Ser Thr Ala Tyr Met His Leu Lys Ser Leu Thr Ser Glu Asp Ser
225                 230                 235                 240

Ala Val Tyr Tyr Cys Val Ser Gly Met Glu Tyr Trp Gly Gln Gly Thr
                245                 250                 255

Ser Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485
```

<210> SEQ ID NO 12
<211> LENGTH: 1458
<212> TYPE: DNA
<213> ORGANISM: Artificial Sequence
<220> FEATURE:
<223> OTHER INFORMATION: nucleotide sequence of 14G2a-CAR

<400> SEQUENCE: 12

```
atggcactgc cagtcaccgc actgctgctg ccactcgcac tgctcctgca tgccgctaga     60

ccagacgtgg tgatgaccca gactcctctg agcctcccag tgtctctggg agatcaggct    120

tccataagtt gcagatccag ccagtcactc gtccacagga atggtaacac ctacctccac    180

tggtacctgc aaaagcctgg tcagtctcca aagctcctga ttcacaaggt ttccaataga    240

ttcagtggcg tgccagaccg gttttccggc tcagggagtg gcaccgactt cacactcaag    300
```

-continued

```
atcagtcggg tggaggccga ggatctcggc gtctactttt gctctcagtc cacacacgtt    360

ccacctctca cctttggagc tggtacaaag ctggagctga aaggaggagg cggctctggc    420

ggaggtggct ccggtggtgg cgggagcgag gttcagctgc tccagagcgg acctgagctc    480

gagaagccct ctgctagcgt gatgatctct tgtaaggctt ccggcagtag ctttaccggg    540

tacaacatga attgggttag gcagaacata gggaaatctc tggaatggat cggagctatc    600

gatccctatt acggtggcac tagttacaac caaaagttca agggacgcgc tactctcaca    660

gtcgataaga gctccagtac tgcatacatg cacctcaagt ctctcacatc cgaagatagc    720

gccgtgtact attgcgtcag cgggatggag tattgggggc agggaacctc cgttaccgtt    780

tcttctacaa ctactccagc tccaagacct ccaactcctg caccaaccat cgcttctcag    840

cctctgtctc tgagacccga ggcttgcagg ccagccgcag gaggagcagt tcatactcgc    900

ggcctcgatt tcgcatgtga tatctacatc tgggctccac tggcaggcac ctgtggagtt    960

ctgctgctga gcctggtgat cactctgtat tgtaagagag gtagaaagaa gctgctgtac   1020

atctttaagc agcccttat gcgccctgtt cagacaacac aggaggaaga tgggtgctca   1080

tgcaggttcc cagaggagga agagggaggg tgcgagctga gggtcaagtt ttctcggagc   1140

gctgacgcac ctgcctatca gcagggtcag aatcagctgt acaacgagct caatctcggc   1200

agacgcgagg agtacgacgt gctcgataaa cggcgcggtc gggaccctga aatgggaggt   1260

aagcctcgca ggaagaaccc acaggagggt ctgtacaacg aactgcagaa agacaagatg   1320

gctgaggcct acagcgagat tggcatgaag ggcgagagga ggagaggaaa aggccatgac   1380

ggcctgtatc agggtctgtc tactgcaact aaggatacct atgatgccct gcacatgcag   1440

gctctcccac ccagataa                                                 1458


<210> SEQ ID NO 13
<211> LENGTH: 1071
<212> TYPE: PRT
<213> ORGANISM: Artificial Sequence
<220> FEATURE:
<223> OTHER INFORMATION: amino acid sequence of 14G2a-CAR-7x2b

<400> SEQUENCE: 13

Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Arg Asn Gly Asn Thr Tyr Leu His Trp Tyr Leu Gln
    50                  55                  60

Lys Pro Gly Gln Ser Pro Lys Leu Leu Ile His Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110

Phe Cys Ser Gln Ser Thr His Val Pro Pro Leu Thr Phe Gly Ala Gly
        115                 120                 125

Thr Lys Leu Glu Leu Lys Gly Gly Gly Gly Ser Gly Gly Gly Ser
    130                 135                 140

Gly Gly Gly Gly Ser Glu Val Gln Leu Leu Gln Ser Gly Pro Glu Leu
145                 150                 155                 160
```

```
Glu Lys Pro Ser Ala Ser Val Met Ile Ser Cys Lys Ala Ser Gly Ser
                165                 170                 175

Ser Phe Thr Gly Tyr Asn Met Asn Trp Val Arg Gln Asn Ile Gly Lys
            180                 185                 190

Ser Leu Glu Trp Ile Gly Ala Ile Asp Pro Tyr Tyr Gly Gly Thr Ser
        195                 200                 205

Tyr Asn Gln Lys Phe Lys Gly Arg Ala Thr Leu Thr Val Asp Lys Ser
    210                 215                 220

Ser Ser Thr Ala Tyr Met His Leu Lys Ser Leu Thr Ser Glu Asp Ser
225                 230                 235                 240

Ala Val Tyr Tyr Cys Val Ser Gly Met Glu Tyr Trp Gly Gln Gly Thr
                245                 250                 255

Ser Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg Ser Gly Ser Gly Pro Gly Ala Thr Asn Phe Ser
                485                 490                 495

Leu Leu Lys Gln Ala Gly Asp Val Glu Glu Asn Pro Gly Pro Met Phe
            500                 505                 510

His Val Ser Phe Arg Tyr Ile Phe Gly Leu Pro Pro Leu Ile Leu Val
        515                 520                 525

Leu Leu Pro Val Ala Ser Ser Asp Cys Asp Ile Glu Gly Lys Asp Gly
    530                 535                 540

Lys Gln Tyr Glu Ser Val Leu Met Val Ser Ile Asp Gln Leu Leu Asp
545                 550                 555                 560

Ser Met Lys Glu Ile Gly Ser Asn Cys Leu Asn Asn Glu Phe Asn Phe
                565                 570                 575
```

-continued

```
Phe Lys Arg His Ile Cys Asp Ala Asn Lys Glu Gly Met Phe Leu Phe
            580                 585                 590

Arg Ala Ala Arg Lys Leu Arg Gln Phe Leu Lys Met Asn Ser Thr Gly
        595                 600                 605

Asp Phe Asp Leu His Leu Leu Lys Val Ser Glu Gly Thr Thr Ile Leu
    610                 615                 620

Leu Asn Cys Thr Gly Gln Val Lys Gly Arg Lys Pro Ala Ala Leu Gly
625                 630                 635                 640

Glu Ala Gln Pro Thr Lys Ser Leu Glu Glu Asn Lys Ser Leu Lys Glu
                645                 650                 655

Gln Lys Lys Leu Asn Asp Leu Cys Phe Leu Lys Arg Leu Leu Gln Glu
            660                 665                 670

Ile Lys Thr Cys Trp Asn Lys Ile Leu Met Gly Thr Lys Glu His Gly
        675                 680                 685

Ser Ala Ser Arg Gly Glu Gly Arg Gly Ser Leu Leu Thr Cys Gly Asp
    690                 695                 700

Val Glu Glu Asn Pro Gly Pro Met Leu Ser Thr Ser Arg Ser Arg Phe
705                 710                 715                 720

Ile Arg Asn Thr Asn Glu Ser Gly Glu Glu Val Thr Thr Phe Phe Asp
                725                 730                 735

Tyr Asp Tyr Gly Ala Pro Cys His Lys Phe Asp Val Lys Gln Ile Gly
            740                 745                 750

Ala Gln Leu Leu Pro Pro Leu Tyr Ser Leu Val Phe Ile Phe Gly Phe
        755                 760                 765

Val Gly Asn Met Leu Val Val Leu Ile Leu Ile Asn Cys Lys Lys Leu
    770                 775                 780

Lys Cys Leu Thr Asp Ile Tyr Leu Leu Asn Leu Ala Ile Ser Asp Leu
785                 790                 795                 800

Leu Phe Leu Ile Thr Leu Pro Leu Trp Ala His Ser Ala Ala Asn Glu
                805                 810                 815

Trp Val Phe Gly Asn Ala Met Cys Lys Leu Phe Thr Gly Leu Tyr His
            820                 825                 830

Ile Gly Tyr Phe Gly Gly Ile Phe Phe Ile Ile Leu Leu Thr Ile Asp
        835                 840                 845

Arg Tyr Leu Ala Ile Val His Ala Val Phe Ala Leu Lys Ala Arg Thr
    850                 855                 860

Val Thr Phe Gly Val Val Thr Ser Val Ile Thr Trp Leu Val Ala Val
865                 870                 875                 880

Phe Ala Ser Val Pro Gly Ile Ile Phe Thr Lys Cys Gln Lys Glu Asp
                885                 890                 895

Ser Val Tyr Val Cys Gly Pro Tyr Phe Pro Arg Gly Trp Asn Asn Phe
            900                 905                 910

His Thr Ile Met Arg Asn Ile Leu Gly Leu Val Leu Pro Leu Leu Ile
        915                 920                 925

Met Val Ile Cys Tyr Ser Gly Ile Leu Lys Thr Leu Leu Arg Cys Arg
    930                 935                 940

Asn Glu Lys Lys Arg His Arg Ala Val Arg Val Ile Phe Thr Ile Met
945                 950                 955                 960

Ile Val Tyr Phe Leu Phe Trp Thr Pro Tyr Asn Ile Val Ile Leu Leu
                965                 970                 975

Asn Thr Phe Gln Glu Phe Phe Gly Leu Ser Asn Cys Glu Ser Thr Ser
            980                 985                 990

Gln Leu Asp Gln Ala Thr Gln Val  Thr Glu Thr Leu Gly  Met Thr His
```

```
        995                 1000                1005

Cys Cys  Ile Asn Pro Ile Ile  Tyr Ala Phe Val Gly  Glu Lys Phe
    1010                 1015                 1020

Arg Arg  Tyr Leu Ser Val Phe  Phe Arg Lys His Ile  Thr Lys Arg
    1025                 1030                 1035

Phe Cys  Lys Gln Cys Pro Val  Phe Tyr Arg Glu Thr  Val Asp Gly
    1040                 1045                 1050

Val Thr  Ser Thr Asn Thr Pro  Ser Thr Gly Glu Gln  Glu Val Ser
    1055                 1060                 1065

Ala Gly  Leu
    1070


<210> SEQ ID NO 14
<211> LENGTH: 3216
<212> TYPE: DNA
<213> ORGANISM: Artificial Sequence
<220> FEATURE:
<223> OTHER INFORMATION: nucleotide sequence of 14G2a-CAR-7x2b

<400> SEQUENCE: 14

atggcactgc cagtcaccgc actgctgctg ccactcgcac tgctcctgca tgccgctaga     60

ccagacgtgg tgatgaccca gactcctctg agcctcccag tgtctctggg agatcaggct    120

tccataagtt gcagatccag ccagtcactc gtccacagga atggtaacac ctacctccac    180

tggtacctgc aaaagcctgg tcagtctcca aagctcctga ttcacaaggt ttccaataga    240

ttcagtggcg tgccagaccg gttttccggc tcagggagtg gcaccgactt cacactcaag    300

atcagtcggg tggaggccga ggatctcggc gtctactttt gctctcagtc cacacacgtt    360

ccacctctca cctttggagc tggtacaaag ctggagctga aaggaggagg cggctctggc    420

ggaggtggct ccggtggtgg cgggagcgag gttcagctgc tccagagcgg acctgagctc    480

gagaagccct ctgctagcgt gatgatctct tgtaaggctt ccggcagtag ctttaccggg    540

tacaacatga attgggttag gcagaacata gggaaatctc tggaatggat cggagctatc    600

gatccctatt acggtggcac tagttacaac caaaagttca agggacgcgc tactctcaca    660

gtcgataaga gctccagtac tgcatacatg cacctcaagt ctctcacatc cgaagatagc    720

gccgtgtact attgcgtcag cgggatggag tattgggggc agggaacctc cgttaccgtt    780

tcttctacaa ctactccagc tccaagacct ccaactcctg caccaaccat cgcttctcag    840

cctctgtctc tgagacccga ggcttgcagg ccagccgcag gaggagcagt tcatactcgc    900

ggcctcgatt tcgcatgtga tatctacatc tgggctccac tggcaggcac ctgtggagtt    960

ctgctgctga gcctggtgat cactctgtat tgtaagagag gtagaaagaa gctgctgtac   1020

atctttaagc agccctttat gcgccctgtt cagacaacac aggaggaaga tgggtgctca   1080

tgcaggttcc cagaggagga agagggaggg tgcgagctga gggtcaagtt ttctcggagc   1140

gctgacgcac ctgcctatca gcagggtcag aatcagctgt acaacgagct caatctcggc   1200

agacgcgagg agtacgacgt gctcgataaa cggcgcggtc gggaccctga aatgggaggt   1260

aagcctcgca ggaagaaccc acaggagggt ctgtacaacg aactgcagaa agacaagatg   1320

gctgaggcct acagcgagat tggcatgaag ggcgagagga ggagaggaaa aggccatgac   1380

ggcctgtatc agggtctgtc tactgcaact aaggatacct atgatgccct gcacatgcag   1440

gctctcccac ccagatccgg atccggacct ggcgctacta acttttctct cctgaagcaa   1500

gctggtgatg tcgaggaaaa ccctggacca atgtttcacg tctcctttcg gtatatcttt   1560
```

-continued

```
ggactgcctc cactcattct ggtcctgctg ccagtggcct cttcagattg tgacattgag   1620
ggtaaggatg gtaaacagta cgagtctgtc ctgatggtta gcattgacca gctcctcgac   1680
tctatgaaag agattggttc taattgcctg aataacgagt tcaacttctt caagaggcat   1740
atctgcgacg ccaataagga aggtatgttt ctcttcagag ctgctagaaa gctgcgccag   1800
ttcctgaaga tgaactccac aggcgatttt gacctccacc tgctcaaagt ctcagaggga   1860
actactattc tgctgaattg tactggccag gtgaagggca gaaagccagc agcactgggt   1920
gaggctcagc ccactaagtc actggaagag aacaagagcc tgaaagaaca aaagaaactc   1980
aacgacctgt gctttctcaa aagactgctc caggagatca aaacctgctg gaataagatt   2040
ctgatgggca ctaaggagca cggttcagca tctagaggag agggtagagg aagtctgctc   2100
acctgtggag atgttgaaga aaaccccggg cctatgctgt ccacaagtag gagccgcttc   2160
atcagaaata caaacgaatc tggagaagag gttaccacat tctttgacta cgattatggc   2220
gctccatgcc acaagtttga tgtcaaacag ataggtgctc aactcctgcc acctctgtat   2280
agcctcgttt tcatcttcgg cttcgtggga aatatgctcg tggtgctgat tctgattaac   2340
tgtaagaaac tgaaatgcct gaccgacatc tacctcctca acctcgccat tagcgacctg   2400
ctgtttctga ttaccctccc tctgtgggca catagtgctg caaatgaatg ggtgttcggt   2460
aacgctatgt gcaaactctt tacagggctc tatcacattg ggtactttgg cggtatcttc   2520
ttcatcatcc tgctcaccat agaccggtat ctggctatcg ttcatgccgt gttcgccctg   2580
aaggctagga cagtgacctt tggagttgtg acaagtgtta tcacttggct ggtcgcagtg   2640
ttcgccagtg tgccagggat catctttacc aaatgccaga aggaagattc agtgtacgtc   2700
tgcggaccat acttccctag aggttggaat aatttccaca ccataatgcg caacatcctg   2760
ggactcgtgc tgccactgct gatcatggtg atttgttact caggcatcct gaaaaccctg   2820
ctccgctgcc ggaacgagaa gaaacggcat agggcagtga gggttatatt cacaatcatg   2880
atcgtgtact ttctgttctg gacaccttac aacattgtga tactcctgaa cactttccaa   2940
gagttcttcg gtctgtctaa ctgtgaaagc accagccaac tcgaccaagc aacccaggtt   3000
actgagacac tgggcatgac acactgttgc atcaatccta tcatatacgc atttgttggc   3060
gagaaatttc ggagatacct ctcagtgttc ttcagaaaac acataactaa gaggttctgt   3120
aaacagtgcc ctgtcttcta tcgcgagaca gtggatggag tgacaagcac caatactcct   3180
tctaccggag aacaggaggt gtccgcagga ctgtaa                              3216
```